US006875602B2

(12) United States Patent
Gutierrez (10) Patent No.: US 6,875,602 B2
(45) Date of Patent: Apr. 5, 2005

(54) PORTABLE THERMOCYCLER (75) Inventor: Anthony G. Gutierrez, Stewartstown, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/668,365

(22) Filed: Sep. 24, 2003

(65) Prior Publication Data

US 2004/0115799 A1 Jun. 17, 2004

Related U.S. Application Data (60) Provisional application No. 60/412,802, filed on Sep. 24, 2002.

(51) Int. Cl.[7] ............................................... C12M 1/38
(52) U.S. Cl. ............................. 435/286.2; 435/287.2; 435/287.3; 435/303.1; 435/809; 422/99; 422/64; 422/65
(58) Field of Search ......................... 435/286.1, 288.2, 435/287.2, 287.3, 303.1, 809; 422/63–65, 99, 104; 219/389, 325, 428, 462.1

(56) References Cited

U.S. PATENT DOCUMENTS 5,525,300 A * 6/1996 Danssaert et al. ............ 422/99
6,448,066 B1 * 9/2002 Wheatcroft .............. 435/287.2

FOREIGN PATENT DOCUMENTS

CA      2255850      12/1999
JP      06277036 A * 10/1994 ............ C12M/1/00

OTHER PUBLICATIONS

"Appendix B: How a Peltier Heat Pum Works", printed from www.mir.com/html/support/manuals/opt man/ on Apr. 18, 2002, MJ Research Inc.
"DNA Engine Thermal Cycler Alpha Units", printed from www.mjr.com/html/Instruments/alphas/alphas.html on Mar. 19, 2002, MJ Research Inc.
"Patent and Licensing Information", printed from www.mjr.com/html/support/licenses.html on Mar. 19, 2002, MJ Research Inc.
"RoboCycler Temperature Cyclers and Accessories", Stratagene, Inc. LaJolla, CA, no date provided.
"Some Like It Hot: A Thermal Cycler Roundup", printed from www.the–scientist.com/yr2001/dec/profile 011210.html. on Mar. 19, 2002, The Scientist.

* cited by examiner

Primary Examiner—William H. Beisner
(74) Attorney, Agent, or Firm—Elizabeth Arwine (57) ABSTRACT This invention relates to a portable thermocycler having a unique geometric configuration, which allows the device to be made durable, compact and adapted for field-use. In general, the device includes a case, a rotary plate having a plurality of constant temperature heating blocks and a plurality of sample wheels, wherein the wheels are rotatable and pivotable to allow a plurality of reaction vessels, organized in cassettes, to be moved into contact with the heating blocks for heat transfer applications.

15 Claims, 4 Drawing Sheets

PORTABLE THERMOCYCLER

This application claims the benefit of priority under 35 U.S.C. § 119(e) from U.S. Ser. No. 60/412,802, filed on Sep. 24, 2002.

I. FIELD OF THE INVENTION

This present invention relates to thermal cyclers, or "thermocyclers." More particularly, the present invention relates to novel portable thermocyclers.

II. DESCRIPTION OF THE RELATED ART

Systems which require multiple or cyclic chemical reactions to produce a desired product often require careful temperature control to produce optimal results. Such reactions include nucleic acid amplification reactions such as the polymerase chain reaction (PCR) and the ligase chain reaction (LCR).

Consider PCR for instance. PCR is a technique involving multiple cycles that results in the geometric amplification of certain polynucleotide sequences each time a cycle is completed. The technique of PCR is well known to the person of average skill in the art of molecular biology. The technique of PCR is described in many books, including, "PCR: A Practical Approach," M. J. McPherson, et al., IRL Press (1991), "PCR Protocols: A Guide to Methods and Applications," by Innis, et al., Academic Press (1990), and "PCR Technology: Principals and Applications for DNA Amplification," H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, which are hereby incorporated by reference for the purpose of providing examples of PCR devices and techniques.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle.

As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

The temperature of the reaction mixture must be varied during a PCR cycle, and consequently varied many times during a multicycle PCR experiment. For example, denaturation of DNA typically takes place at around 90 degrees to 95 degrees C., annealing a primer to the denatured DNA is typically performed at around 40 degrees to 60 degrees C., and the step of extending the annealed primers with a polymerase is typically performed at around 70 degrees to 75 degrees C.

For this reason, apparatuses have been developed which permit the accurate control of the temperature of reaction vessels in which such amplification reactions are performed.

For example, there are a number of thermal "cyclers" used for DNA amplification and sequencing in the prior art in which one or more temperature controlled elements or "blocks" hold the reaction mixture, and the temperature of a block is varied over time. As will be appreciated, these devices suffer from several drawbacks. For example, these devices require a strong power source, typically from an external source, such as electrical outlets, due to the energy required to raise and lower the temperature of the heating blocks. Accordingly, these devices cannot be adapted for field use.

In an effort to overcome the need to raise and lower the temperature of the heating blocks, other prior artisans have devised a system known as a temperature cycler. In this system, multiple temperature controlled blocks are kept at different desired temperatures and a robotic arm is utilized to move reaction mixtures from block to block. However, as will be appreciated, these systems suffer from their own set of drawbacks. For example, these systems typically only allow one of the heating blocks to be used at any given time.

An exemplary temperature cycler is exhibited by the RoboCycler manufactured by Stratagene. The RoboCycler has four stations, but only one batch of samples is processed at a given time. The preferred operation for the RoboCycler appears to be for a single robot arm to move the single sample batch from station to station pursuant to a pattern previously inputted by a user or stored in memory. As will be appreciated, these devices are slow and inefficient.

Furthermore, as will be appreciated by one of ordinary skill in the art, these prior art devices are very cumbersome and have fragile components, which make them ill-suited for field use.

The foregoing underscores some of the problems associated with conventional thermocycler devices. Furthermore, the foregoing highlights the need in the art for a portable, durable and efficient thermocycler adaptable for field use.

III. SUMMARY OF THE INVENTION

The present invention overcomes the aforementioned drawbacks and offers new advantages as well.

Accordingly, one object of the invention is to provide a portable thermocycler. Likewise, another object of the invention is to provide a rotary fixed temperature thermocycler.

According to one aspect of the invention, the thermocycler serves as a portable device for use in field situations or where no electrical outlets are available. According to another aspect of the invention, the thermocycler serves as a portable DNA amplification device for field-use.

According to these aspects of the invention, there is provided a three-temperature thermal cycler which utilizes set temperature blocks in a geometric pattern configured to allow samples in capillary cassettes to be rotated into contact with each of the three heating blocks in repeated cycles. This aspect of the invention is based, in part, on the discovery that the use of heating blocks of constant temperature in conjunction with multiple sample cassettes in clusters that are rotatable to the blocks, the durability, compactability and efficiency of the device is greatly enhanced.

According to an aspect of the invention, there is provided a portable DNA amplification device comprising a case, a rotary plate and a plurality of reaction vessels disposed in cassette packs and arranged in cassette clusters. According to this aspect of the invention, the case houses the rotary plate and cassette clusters when in use. In a presently preferred embodiment, the case has a power source for the device. Alternatively, a remote power source may be provided for supplying power to the device.

According to a preferred embodiment, the case includes multiple touchpads to control the operation of the device. As will be appreciated, the use of touchpads decreases the risk that a part may break off the case during transport or field use. In a preferred embodiment, the case includes a display, preferably a digital display, adapted to provide a user with the temperature values and/or the number of cycles for the procedure. In another preferred embodiment, the device includes an LED display adapted to communicate information relating to conditions and results of a procedure to a user.

According to a preferred embodiment, the rotary plate comprises a center heating block and a plurality of outside heating blocks. Preferably, there are six heating blocks arranged in a hexagonal pattern about the central heating block. Heating blocks preferably include a heat source. In a presently preferred embodiment, the heat source comprises a Peltier heat pump (or thermoelectric module) adapted to provide heat to the faces of heater blocks sufficient to perform a PCR procedure.

In a presently preferred embodiment, the central block has six outside faces defining a hexagon, each face having a temperature from about 90 to 100 degrees, preferably 95 degrees. In this embodiment, the six outside heating blocks each have two faces, wherein the two faces of a first block are about 50 to 60 degrees, preferably 55 degrees, and the two faces of the two adjacent blocks are about 70 to 75 degrees, preferably 72 degrees. Accordingly, every other block has faces about 72 degrees and the intermittent blocks have faces about 55 degrees.

According to a preferred embodiment, a rotary plate includes a plurality of rotating wheels adapted to rotate samples, preferably arranged in cassettes, into contact with the various faces of the heating blocks. In a presently preferred embodiment, rotary plate includes six rotating tri-lobed wheels fixed to cooperating tri-lobed cams. Preferably, cams have an engineered rotational wobble, which preferably comprises a duplicate tri-lobed cam (or wheel).

According to an embodiment of the invention, capillary tubes containing product for DNA amplification may be arranged in packs, or cassettes, of six. Preferably, each capillary cassette is coupled to a clip, which facilitates the coupling of the cassette to one of the lobes of one of the tri-lobed wheels.

According to this embodiment of the invention, each tri-lobed wheel is capable of accepting three cassettes, thereby forming a cassette cluster. According to the invention, this configuration allows for 18 capillary tubes (in 3 cassettes of 6 tubes) to be loaded on each of the 6 tri-lobed wheels (3 cassettes per wheel), allowing each of the 108 faces of the hexagonal arrangement of heating faces of the device to be in contact with a capillary cassette. Accordingly, 108 capillary tubes or reaction vessels can be treated at one time and no excess heat is wasted because each face is engaged at all relevant times. However, one of ordinary skill in the art will appreciate that any number of tubes may be treated at one time, and any suitable geometrical configuration of heat blocks may be used in connection with the present invention.

According to a presently preferred embodiment of the invention, rotary plate is rotated by means of cooperating gears. Preferably, six meshed gears cooperate to drive cassette clusters around central heating block. According to the invention, any one of the gears may be associated with a power source, such as a stepper motor, to cause the rotation of all the cooperating gears. As will be appreciated, this means of power and rotation allows for the device to be small, light and portable.

Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements.

V. DETAILED DESCRIPTION OF THE INVENTION

The present invention is based, in part, on the discovery that the use of heating blocks of constant temperature in conjunction with multiple sample cassettes in clusters that are rotatable to the blocks, the durability, compactability and efficiency of a device can be greatly improved.

While the present invention will be described in connection with a rotary fixed temperature DNA amplification device, it will be readily apparent to one of ordinary skill in the art that the present invention can be applied to a multiplicity of fields and uses. In general, the present invention may be used in any field for any task requiring a plurality of heating/cooling zones be applied to a work piece.

The present invention is particularly suited for adaptation of devices for field uses, or other applications wherein an electrical power source is unavailable or impractical.

Figure 1:
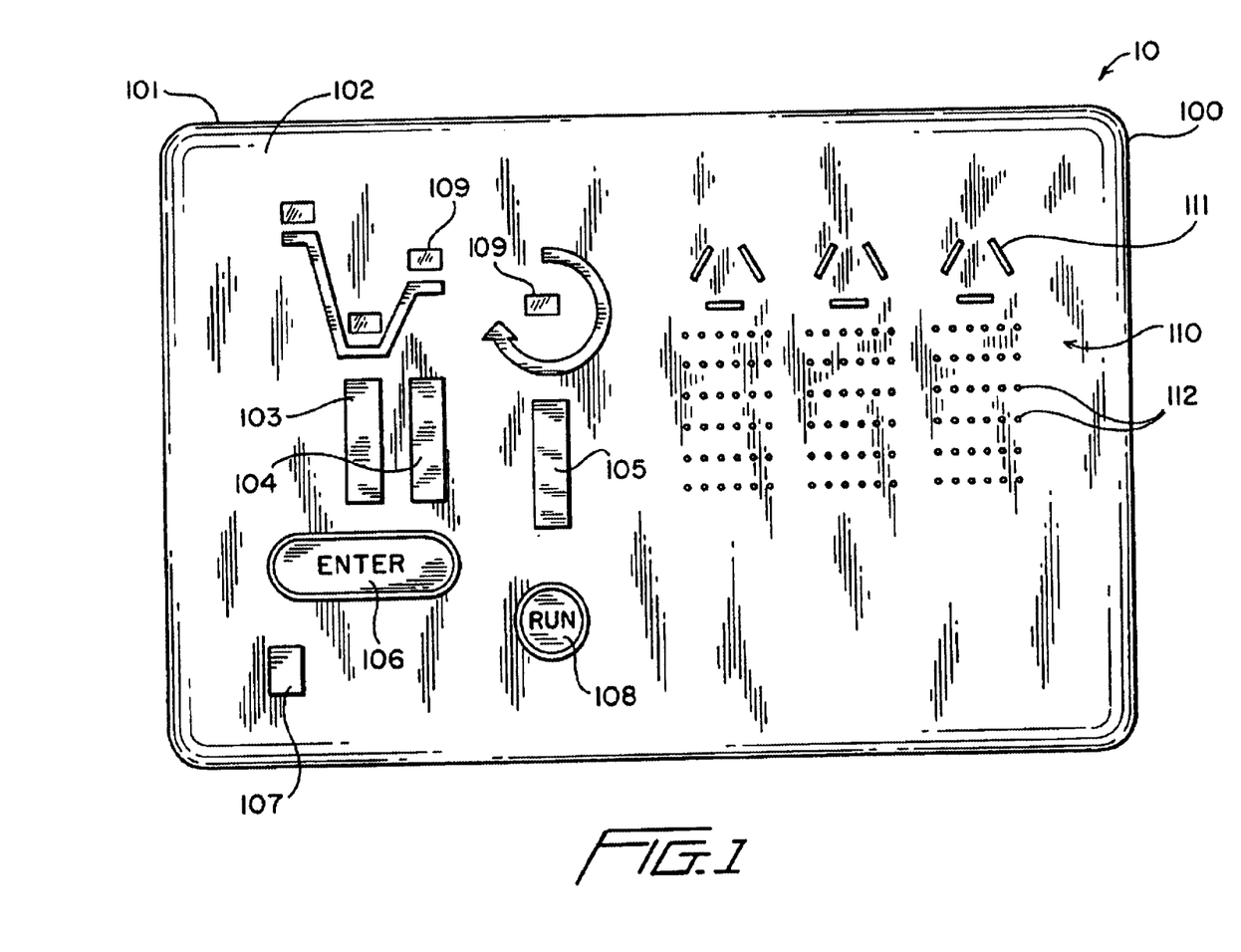
FIG. 1 illustrates a thermocycler case in the closed position according to an embodiment of the invention.

A presently preferred embodiment of the invention is depicted in FIGS. 1–4. In this embodiment of the invention, the device comprises a rotary fixed temperature thermocycler 10 configured for use as a field-ready DNA amplification unit. As depicted in FIG. 1, the device 10 comes packaged in closable case 100. Preferably, case 100 has a hinged lid 101 or other means, which allows for easy access to the case's interior compartment, while also allowing for the lid 101 to be safely secured from incidental opening.

Although it will be readily appreciated that the case 100 can be of any size or shape, the overall device 10 is preferably of a suitable size and weight to maintain the unit's portability such as on the scale of a laptop computer. Case 100 is also preferably constructed of materials, such as lightweight shattered-proof materials, which can withstand the physical shock and field conditions the device may encounter.

As depicted in FIG. 1, case 100 preferably includes multiple touchpads to control the operation of the device as described herein. Although the touchpads can be deployed at any suitable location on the case, it is preferred that the touchpads be located on a top surface 102 of the case 100 to allow a user to easily manipulate the touchpads while allowing the device 10 to lie flat. As will be appreciated, the use of touchpads to control the device is not mandatory, however, touchpads decrease the risk that a lever or switch control will break-off or be damaged during transit or in the field.

As depicted in FIG. 1, it is advantageous to include at least an annealing temperature control touchpad 103, an extension temperature control touchpad 104, and a cycle number touchpad control 105. Preferably, there are additional buttons or touchpads on the control panel, or elsewhere, to aid a user's operation of the device. For example, the device may be provided with an "Enter" button or touchpad 106, which allows the user to enter temperature values and cycle numbers for a procedure. Also, it is preferable to provide an "On/Off" control 107 to operate the power of the device and a "Start" control 108 to allow a user to begin a thermocycle procedure.

Preferably, the device also includes a display 109, preferably a digital display, to provide a user with a visual display of valuable information, for example, the temperatures and number of cycles for the next procedure, or any other useful information.

Preferably, the device also includes an LED array 110 to provide information to a user. LED array 110 may be disposed in any suitable area and or any suitable configuration sufficient to communicate information to a user by any suitable means. In this embodiment, the LED array 110 includes dashes 111 and rows of circles 112. The three sets of dashes 111 are preferably arranged in a geometric pattern, here a triangular pattern, to allow a user to discern the heating block temperatures without having to open the lid 101. For example, a dash in a particular position within a triangle represents that the heating block is at a particular temperature.

Each row of circular LEDs 112 preferably represents a set of sample cassettes on a particular cluster and is adapted to communicate relevant information regarding the results of a procedure without a user having to open the lid 101. For example, the circular LEDs 112 may provide an indication as to the results for a set of samples after completion of PCR, wherein a lit LED indicates a positive result and an unlit LED indicates a negative result (or alternatively, no sample, for instance).

The LED information may be provided by any suitable manner. In a presently preferred embodiment, the information is provided from fiber optics wired in the lid and having a detector positioned above a respective sample and an LED at the opposite end to provide the information regarding the results. The detector preferably detects the presence or lack of presence of a marker's red fluorescent emission after completion of a PCR procedure.

Although not shown, case 100 preferably houses the power source for the device, such as a battery pack. Alternatively, a remote power source may be provided for supplying power to the device.

Figure 2:
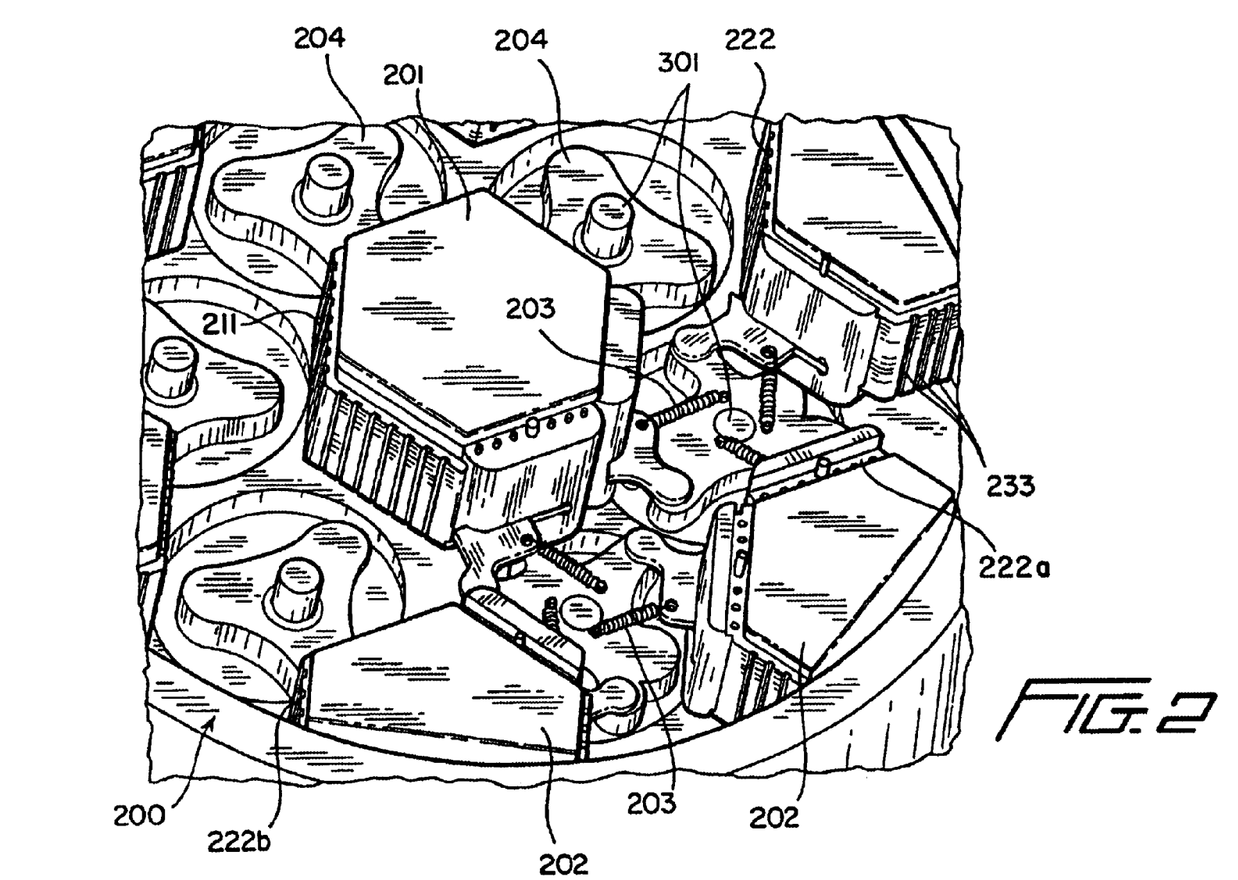
FIG. 2 illustrates a rotary plate and a pair of cassette clusters in operation in a thermocycler according to an embodiment of the invention.

As best depicted in FIG. 2, the inside of case 100 comprises rotary plate 200. In this embodiment, rotary plate 200 has a honeycomb configuration. In this embodiment, rotary plate 200 is patterned in a hexagonal layout. As depicted, for this three-temperature thermocycler, rotary plate 200 comprises a center heating block 201 and a plurality of outside heating blocks 202, in this case six outside heating blocks 202 arranged in a hexagonal pattern about a hexagonal central heating block 201.

All of the heating blocks 201, 202 preferably communicate with heat source (not shown), which is powered by power source (not shown). Although not depicted, in a presently preferred embodiment, the heat source includes a Peltier heat pump (or thermoelectric module) adapted to provide heat to the faces of heat blocks sufficient to perform a PCR procedure.

In this embodiment, central block 201 has six outside faces 211 defining a hexagon, each face 211 having a temperature from about 90 to 100 degrees, preferably 95 degrees. In this embodiment, the six outside heating blocks 202 each have two faces 222, wherein the two faces of a first block 222a are about 50 to 60 degrees, preferably 55 degrees, and the two faces of the two adjacent blocks 222b are about 70 to 75 degrees, preferably 72 degrees. Accordingly, every other block has faces about 72 degrees and the intermittent blocks have faces about 55 degrees.

The faces of heating blocks may include depressions 233 which correspond to reaction vessels that are to be heated, thereby allowing a vessel to be heated on a greater surface area of the vessel.

Rotary plate 200 also includes six rotating tri-lobed wheels 203 fixed to cooperating tri-lobed cams 204. Preferably, cams 204 have an engineered rotational wobble, which preferably is a duplicate tri-lobed cam (or wheel).

Figure 3:
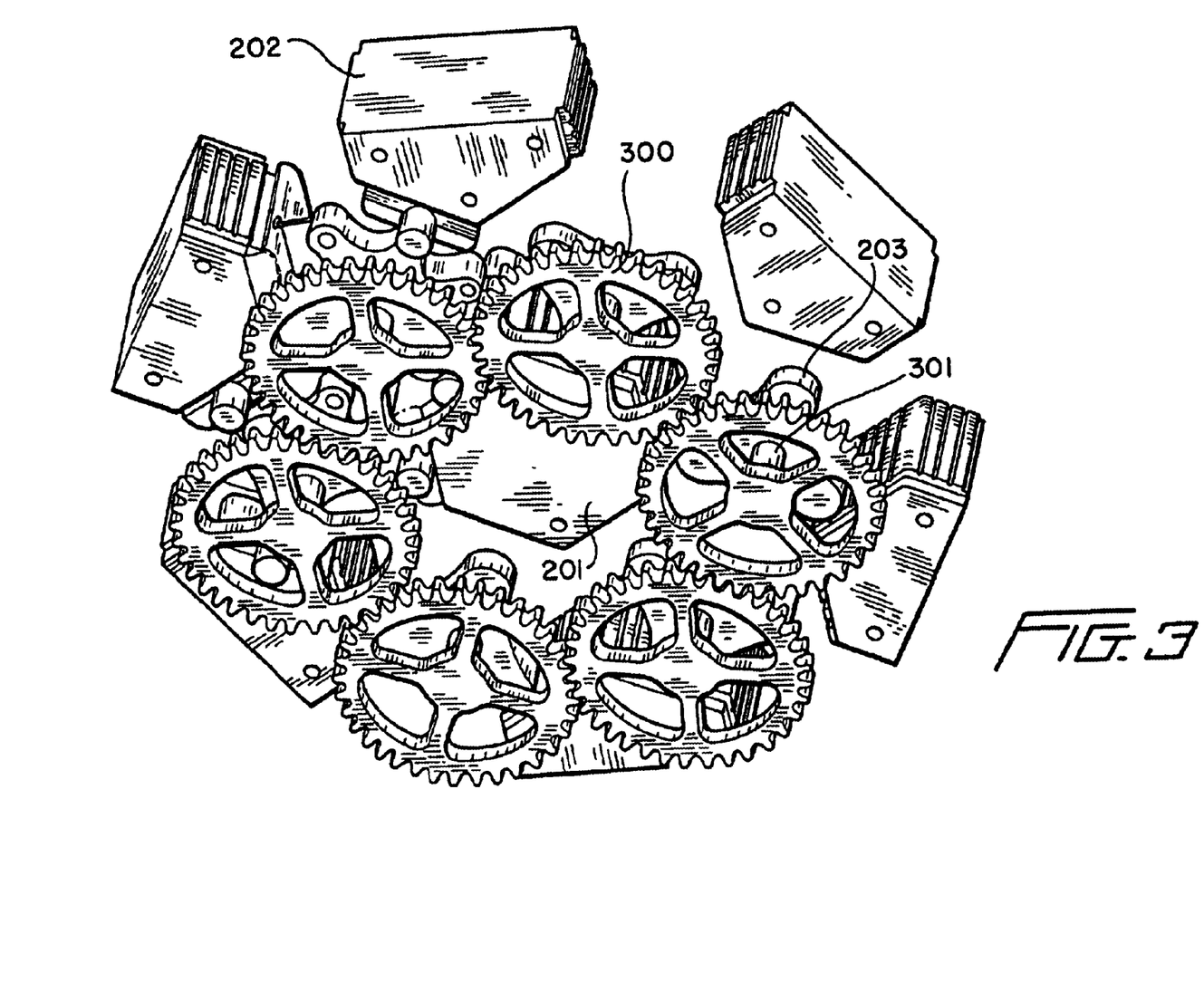
FIG. 3 illustrates the gear configuration and cooperating parts of the rotary plate components with the mounting plate removed for clarity of parts.

As best shown in FIG. 3, meshed gears 300 are used to power and move the rotary plate 200. Each gear preferably includes a spindle 301, which travels through, but does not drive wobble tri-lobed cam 204. Rather, immediately on top of the fixed cam 204 is the tri-lobed sample wheel 203, which is preferably fixed and connected to the spindle 301, whereby gear 300 rotates sample wheel 203.

As will be appreciated, interlocking meshed gears may be moved by applying a force to any one of the gears. Accordingly, a single size and power saving motor, such as a stepper motor, may be provided for powering the rotary plate, while maintaining the light, portable, and efficient nature of the device.

Also as will be appreciated, with a single motor, the calibration of a single gear to ensure, for example, that the device positions samples over each block for 15 seconds, automatically calibrates all others if they have been mounted in synchronization.

If provided, the stepper motor is preferably microprocessor controlled, which allows, for example, a user to use touchpad(s) on the lid to simply input commands, i.e., the number of cycles, etc.

Figure 4:
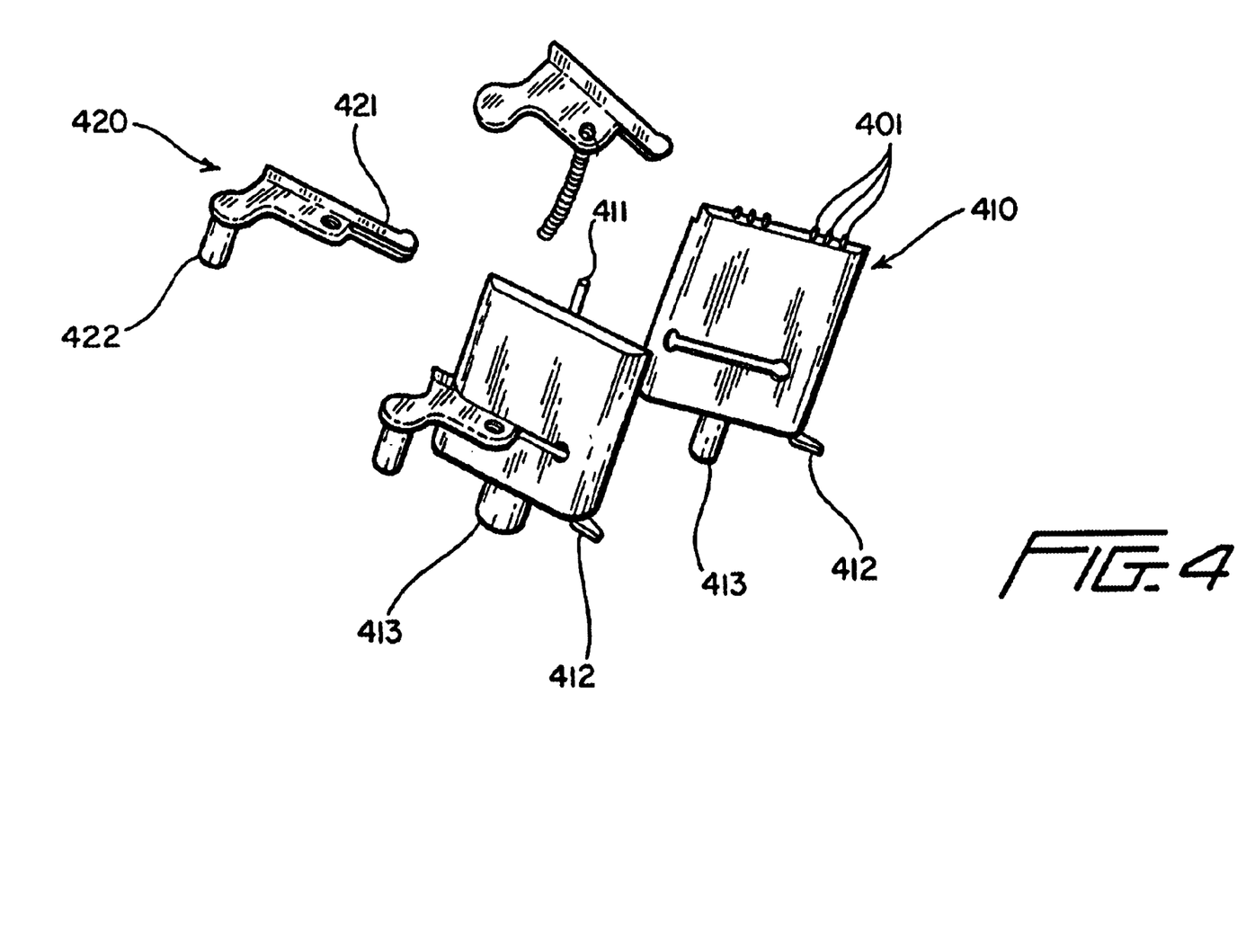
FIG. 4 illustrates a preferred mounting of capillary cassette to a lobe of a tri-lobed wheel to form cassette clusters according to an embodiment of the invention.

According to the embodiment of the invention depicted in FIG. 4, capillary tubes 401 containing product for DNA amplification may be arranged in packs of six in cassettes 410. Cassette 410 may have apertures for accepting tubes 410.

Preferably, each capillary cassette 410 has a top handle 411 to facilitate handling, loading and unloading by a user. Handle 411 may also serve to align cassette 410 with each respective heating block 201, 202 during each engagement to ensure uniform heating.

Cassette 410 also preferably has a dovetail bottom 412 for each capillary tube 401 to keep the capillaries from falling through the cassette 410. At the bottom of the cassette 410 there is also preferably disposed a bearing 413, which allows the cassette 410 to be moved around the fixed cam 204 during movement. The sealed ends of the capillaries 401 are preferably visible at the top of the cassettes 410 to provide the optical access necessary for fluorescent emissions or the like to be detected and the results communicated to the user.

To facilitate mounting of cassette 410 on a lobe of tri-lobed sample wheel 203, a clip 420 is provided. Clip 420 preferably has a resilient end 421 that may be pinched together to allow clip 420 to be inserted into the cassette 410 and then spring back once it reaches a circular space on the cassette 410. Clip 420 also preferably has peg 422 for coupling clip 420 to lobe 203.

In operation, cassettes 410 preferably are normally sprung to be retraced toward the center of the bottom cam 204 allowing free rotation. However, as cassettes 410 rotate to a heating block 201, 202, a smaller roller bearing beneath each cassette 410 preferably rides up the peak of the fixed tri-lobed cam 204 and presses the cassette 410 and its capillary tubes 401 onto the depressions 233 in the respective heating block 201, 202. In a preferred PCR process, cassettes 410 are paused for 15 seconds in each position to allow heat transfer from the block 201, 202 to the contents of the capillary tubes 401 of each cassette 410 to occur.

Preferably, any block surfaces not involved in the heat transfer operation are covered with insulating material. However, in a presently preferred embodiment, during the time of thermal transfer, all positions are preferably simultaneously occupied. The geometric arrangement of the blocks and the unique cam directed movement of the sample cassettes allows for all the temperature controlled surfaces to be used simultaneously. Furthermore, this preferred arrangement allows the entire device to be battery powered for true portability. The entire device may be as small as 2 in.×8 in.×10 in. and may weigh under 10 lbs. A complete DNA amplification reaction could be accomplished in about 20 cycles in a period of about 10–12 minutes.

In a preferred PCR process, each sample passes repeatedly through a sequence of 95 degrees Celsius to 55 degrees Celsius to 72 degrees Celsius for about 20 to 40 cycles (as may be set by the operator). To enable this process, the temperatures of the blocks are set as previously described. In particular, in this embodiment, the central block has six outside faces defining a hexagon, each face having a temperature from about 90 to 100 degrees, preferably 95 degrees and has six outside heating blocks each having two faces, wherein the two faces of a first block are about 50 to 60 degrees, preferably 55 degrees, and the two faces of the two adjacent blocks are about 70 to 75 degrees, preferably 72 degrees. Accordingly, every other block has faces about 72 degrees and the intermittent blocks have faces about 55 degrees.

In operation, with this configuration, the 120 degree rotation from one block to another is performed in about one-half second. Each rotating sample wheel preferably rotates in a direction opposite to adjacent wheels. Accordingly, the 95 degree Celsius block is shared by all six cassette clusters, while the 55 and 72 degree Celsius blocks are shared by adjacent sample clusters.

As will be appreciated, according to this embodiment of the invention, each tri-lobed wheel is capable of accepting three cassettes, thereby forming a cassette cluster. According to the invention, this configuration allows for 18 capillary tubes to be loaded on each of 6 tri-lobed wheels, allowing each of the 108 faces of the hexagonal arrangement of heating faces of the device to be in contact with a capillary pack. Accordingly, 108 capillary tubes can be treated at one time and no excess heat is wasted because each face is engaged at all times. However, one of ordinary skill in the art will appreciate that any number of tubes may be treated at one time, and any suitable geometrical configuration of heat blocks may be used in connection with the present invention. For example, in an alternative embodiment of the invention, the hexagonal matrix of the device is expanded by connecting a similar hexagonal matrix that would share a common periphery heating block 202 with the first hexagonal matrix. Similarly, additional matrices may be added in a modular expansion or by stacking rotary plates on top of each other.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

I claim:

1. A thermocycler device comprising:

a case;

a rotary plate housed in said case;

a plurality of heating blocks having a set temperature disposed in an interior of said rotary plate; and at least one vessel movable relative to said heating blocks and adapted to contact at least two heating blocks;

wherein said temperature blocks are arranged in a geometric pattern configured to allow said at least one vessel to be rotated into contact with each of said heating blocks; and wherein said geometric pattern comprises a central heating block having outside faces defining a hexagon and six outside heating blocks disposed around the periphery of said rotary plate.

2. The thermocycler device of claim 1, wherein said central heating block has a temperature of between about 90 and 95 degrees Celsius, three of said outside heating blocks have a temperature of about 50 to 60 degrees Celsius, and the other three of said outside heating blocks have a temperature of about 70 to 75 degrees Celsius.

3. The thermocycler device of claim 1, wherein said rotary plate includes a plurality of rotating wheels adapted to rotate a plurality of vessels into contact with at least two of said heating blocks.

4. The thermocycler device of claim 3, wherein said temperature blocks are arranged in a geometric pattern configured to allow said vessels to be rotated into contact with each of said heating blocks.

5. A thermocycler device comprising:

a case;

a rotary plate housed in said case;

a plurality of heating blocks having a set temperature disposed in an interior of said rotary plate; and at least one vessel, movable relative to said heating blocks and adapted to contact at least two heating blocks;

wherein said rotary plate includes a plurality of rotating wheels adapted to rotate a plurality of vessels into contact with at least two of said heating blocks;

wherein said temperature blocks are arranged in a geometric pattern configured to allow said vessels to be rotated into contact with each of said heating blocks; and wherein said rotating wheels comprise tri-lobed wheels adapted to accept three vessels carrying cassettes.

6. The thermocycler device of claim 5, wherein said wheels are maneuvered by meshed gears having spindles associated with said wheels.

7. The thermocycler device of claim 6, wherein said rotary plate includes wobble wheels beneath said tri-lobed wheels.

8. The thermocycler device of 7, wherein said geometric pattern comprises a central heating block having outside faces defining a hexagon and six outside heating blocks disposed around the periphery of said rotary plate.

9. The thermocycler device of claim 6, wherein said central heating block has a temperature of between about 90 and 95 degrees Celsius, three of said outside heating blocks have a temperature of about 50 to 60 degrees Celsius, and the other three of said outside heating blocks have a temperature of about 70 to 75 degrees Celsius.

10. The thermocycler device of claim 5, further comprising a power source for said device.

11. The thermocycler device of claim 5, wherein said heating blocks are associated with a heating source.

12. A portable three-temperature thermocycler device for DNA amplification comprising:
   a case; said case having a hinged-lid to enable access to an interior area of said case and being constructed of shock-resistant material;
   a plurality of touchpad controls integral with a top surface of said case;
   a digital display on said top surface of said case, said display adapted to provide visual information;
   a LED display for providing information to a user of the device integral with said top surface of said case;
   a rotary plate disposed in said interior space of said case, said rotary plate having a honeycomb configuration;
   a central heating block disposed centrally in said rotary plate, said central heating block having six faces defining a hexagon;
   six outside heating blocks disposed around the periphery of said rotary plate and defining a hexagonal pattern;
   six tri-lobed wheels, each lobe being configured to be matable with a cassette of capillary vessels, said six wheels being disposed between said central heating block and said outside heating blocks in a circular pattern, wherein said wheels are rotatable around said central block via cooperation with meshed gears on an underside of said rotary plate and being pivotable relative to said heating blocks such that each of said cassettes is capable of being contacted to each of said heating blocks in a repeatable cycle.

13. The device of claim 12, further comprising a wobble cam disposed between said gears and said tri-lobed wheels.

14. The device of claim 13, further comprising means for heating said heating blocks.

15. The device of claim 13, further comprising means for powering said device.

* * * * *

UNITED STATES PATENT AND TRADEMARK OFFICE
CERTIFICATE OF CORRECTION

PATENT NO. : 6,875,602 B2
DATED : April 5, 2005
INVENTOR(S) : Anthony G. Gutierrez It is certified that error appears in the above-identified patent and that said Letters Patent is hereby corrected as shown below:

Column 8,
Line 50, after "vessel" and before "movable" delete ",".

Signed and Sealed this

Twentieth Day of September, 2005

JON W. DUDAS
*Director of the United States Patent and Trademark Office*